United States Patent [19]

Reinhold, Jr. et al.

[11] Patent Number: 4,862,896
[45] Date of Patent: Sep. 5, 1989

[54] MONITORING DEVICE WITH DUAL POSITION ELECTRODES

[75] Inventors: Herbert E. Reinhold, Jr.; Douglas J. Greenwold, both of Rockville, Md.

[73] Assignee: Survival Technology, Inc., Bethesda, Md.

[21] Appl. No.: 172,840

[22] Filed: Mar. 25, 1988

[51] Int. Cl.⁴ .............................................. A61B 5/04
[52] U.S. Cl. .................................... 128/696; 128/904; 128/639
[58] Field of Search ................ 128/696, 709, 904, 639

[56] References Cited

U.S. PATENT DOCUMENTS

| | | | |
|---|---|---|---|
| 3,792,700 | 2/1974 | Sarnoff et al. | 128/639 |
| 3,872,252 | 3/1975 | Malchman et al. | 128/904 |
| 3,885,552 | 5/1975 | Kennedy | 128/904 |
| 3,910,260 | 10/1975 | Sarnoff et al. | 128/639 |
| 3,938,507 | 2/1976 | Sarnoff et al. | 128/701 |
| 4,004,577 | 1/1977 | Sarnoff | 128/710 |
| 4,159,018 | 6/1979 | Brastad | 128/904 |
| 4,535,783 | 8/1985 | Marangoni | 128/711 |
| 4,622,979 | 11/1986 | Katchis et al. | 128/904 |
| 4,658,830 | 4/1987 | Sarnoff | 128/696 |
| 4,686,998 | 8/1987 | Robbins | 128/696 |

FOREIGN PATENT DOCUMENTS

| | | | |
|---|---|---|---|
| 0979073 | 12/1975 | Canada | 128/696 |
| 3040098 | 6/1982 | Fed. Rep. of Germany | 128/696 |

Primary Examiner—Lee S. Cohen
Assistant Examiner—K. Schaetzle
Attorney, Agent, or Firm—Cushman, Darby & Cushman

[57] ABSTRACT

A heart monitoring device for use under emergency conditions including a portable housing, a pair of electrodes and a pair of electrical wires connecting the electrodes to the housing and to an electrical circuit carried therein. The electrodes are usable in two modes. One mode is a precordial mode wherein the electrodes are mounted on the exterior of the housing in spaced positions fixed with respect to the housing in commonly outwardly facing relation so as to be conveniently engageable with the skin of the chest of a user by manually engaging the housing and moving it with the electrodes fixed thereto into housing retained operative positions on the chest skin. The second mode is a non-precordial mode wherein the electrodes are removed from the housing and, preferably, self-retained within the armpits.

9 Claims, 2 Drawing Sheets

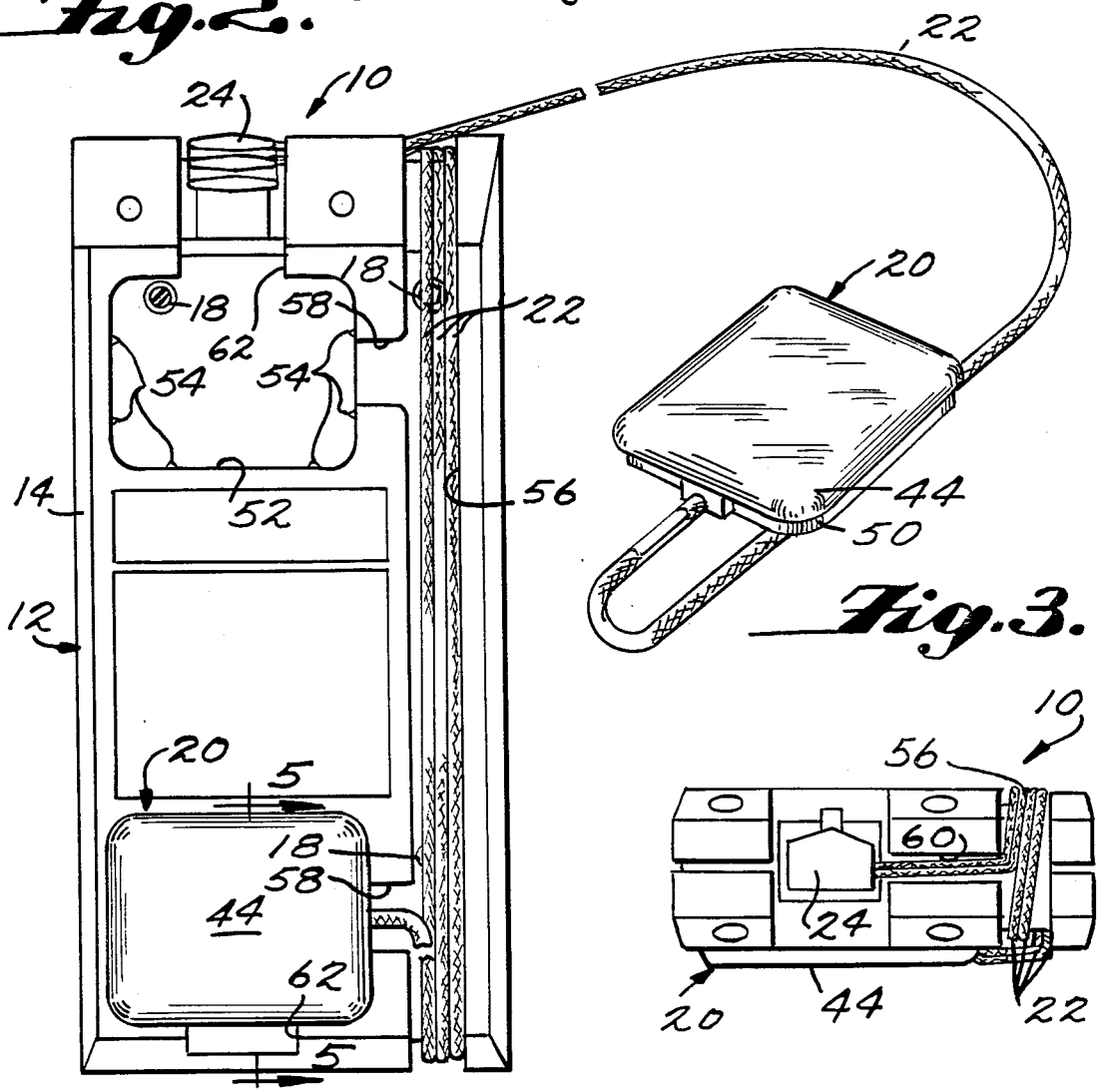

MONITORING DEVICE WITH DUAL POSITION ELECTRODES

This invention relates to heart monitors and, more particularly, to heart monitors of the type described in U.S. Pat. No. 3,938,507.

The monitor disclosed in the aforesaid patent is provided with a pair of electrodes which are configured so as to be conveniently and comfortably held within the armpits of a user in accordance with the teachings of U.S. Pat. No. 3,792,700. A preferred use of the device is in the method disclosed in U.S. Pat. Nos. 3,910,260, 4,004,577, and 4,658,830. As disclosed in the aforesaid patents, the heart monitor may be used in conjunction with medicaments contained with autoinjectors for enabling a designated coronary prone individual to self administer arrythmia and thrombolytic treatment drugs during the early minutes or hours of the onset of heart attack symptoms at a time before the individual can be hospitalized or reached by an ambulance crew.

For this use, it is important that the monitor be capable of simple, but effective, connection with the user so as to acquire the electrical activity of the heart of the user in a form capable of transmission over a telephone line to a central source where sufficient intelligence is provided for aiding the individual in undertaking the self administered treatment.

As indicated, it is important in the operation of a heart monitor of the type which is useful in such emergency situations that the electrodes be capable of simple and convenient connection with the user so as to reliably acquire the electrical activity of the user's heart for transmitting over the telephone line. The utilization of electrodes which are configured to be placed in the armpits of the user provide several advantages. One advantage of the arrangement is that the electrical activity of the heart which is acquired by positioning the electrodes in the armpit is a non-precordial acquisition. This means that the distance between the two electrodes when applied to the individual is significantly greater than the size of the portable monitor housing.

It has been proposed to provide electrodes directly on the monitor housing so as to achieve simple and convenient attachment of the electrodes to the user to acquire the precordial electrical activity of the heart of the user. See, for example, U.S. Pat. No. 4,535,783 dated Aug. 20, 1985. It is also well known to provide separate sets of electrodes two of which are designed for non-precordial acquisition while two others are designed for precordial acquisition. One such device which has been offered to the market but has achieved no significant acceptance involves the use of the monitor of U.S. Pat. No. 3,938,507 with a jacket for containing the monitor. The jacket had built into it a second set of electrodes that were mounted on the jacket in a position similar to the mounting in U.S. Pat. No. 4,535,783. The arrangement required that an electrical connection to the electrodes on the jacket be provided when the monitor was stored in the jacket and had the disadvantage of requiring removal of the jacket when the monitor was to be used in the armpit mode. Accordingly, there still exists a need for a monitor device which can provide both types of connections without the disadvantages noted above and in a cost effective manner.

It is an object of the present invention to fulfill the need noted above. In accordance with the principles of the present invention, this objective is achieved by providing a device suitable for use under emergency conditions for acquiring the electrical activity of the heart of a user in a form suitable for transmission over a telephonic line. The device includes a portable housing, a pair of electrodes operable when positioned in operative contacting relation with the skin of a user to require the electrical activity of the heart of the user, and a pair of elongated electrical wires connected with the electrodes and with the housing for transmitting the electrical activity of the heart of the user acquired by the electrodes to the housing. A sonic speaker is carried by the housing for creating signals indicative of the electrical activity acquired by the electrodes in a form suitable for transmission over a telephonic line and an electric circuit within the housing functions to transmit the electrical activity acquired by the electrodes and transmitted by the pair of electrical wires to the sonic speaker so as to create therein signals indicative of the electrical activity acquired by the electrodes for transmission over a telephonic line. The electrodes are removably mounted on the exterior of the housing in commonly outwardly facing spaced relation with respect to one another in operative positions fixed with respect to the housing wherein the electrodes are movable with the housing and retainable in skin contacting relation with the chest of a user through manual engagement of the housing in housing retained positions thereon to acquire precordial electrical activity of the heart of the user. The electrical wires are mounted on the housing so as to be operable to (1) transmit the precordial electrical activity acquired by the electrodes when in the housing retained positions, (2) enable the electrodes to be manually removed from the operative positions fixed with respect to the housing and extended from the housing into skin contacting relation with the user in directly retained operative positions spaced apart substantially greater than the spacing when in the housing retained positions so as to acquire non-precordial electrical activity of the heart of the user, and (3) transmit the non-precordial electrical activity acquired by the electrodes when in the directly retained operative positions. Preferably, the electrodes are configured to be placed within the armpits of a user and to be comfortably directly retained within the armpits by the user so that the non-precordial heart activity of the heart of the user acquired by the electrodes is between the armpits.

Another object of the present invention is the provision of the type described which is simple in construction, effective in operation, and economical to manufacture.

These and other objects of the present invention will become more apparent during the course of the following detailed description and appended claims.

The invention may best be understood with reference to the accompanying drawings wherein an illustrative embodiment is shown.

In The Drawings:

FIG. 1 is a perspective view of a user retaining a monitor device embodying the principles of the present invention in a precordial position in solid lines and a non-precordial or armpit position in dotted lines;

FIG. 2 is a rear elevational view of the device showing one of the electrodes in its stored precordial position and the other electrode in its removed non-precordial or armpit condition;

FIG. 3 is an end view of the device;

Figure 4:
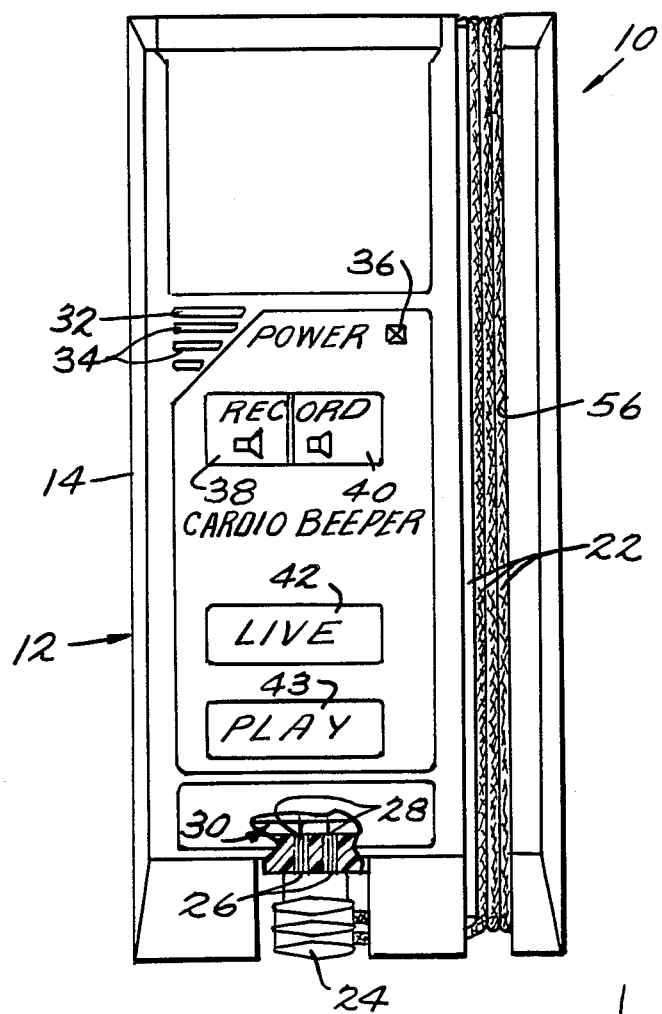
FIG. 4 is a front elevational view of the device with certain parts broken away for purposes of clear illustration.

Referring now more particularly to the drawings, there is shown in FIGS. 2-5 a monitor device, generally indicated at 10, embodying the principles of the present invention which is suitable for use under emergency conditions for acquiring the electrical activity of the heart of a user in a form suitable for transmission over a telephonic line. The device 10 includes a portable housing, generally indicated at 12, which has a width and thickness suitable to be readily grasped in the hand of a user and a length which is sufficient to extend slightly beyond the hand of the user when gripped thereby. The housing 12, as shown, is made up of a front section 14 and a back section 16 held together by suitable fasteners such as the bolts 18 illustrated in FIG. 2. The bolts 18 extend through openings in the back section 16 and threadedly engage within the front section 14.

In accordance with the principles of the present invention, the device 10 also includes a pair of electrodes, generally indicated at 20. A pair of electrical wires 22 is connected at one end with the electrodes 20 and at their opposite end with a plug 24. As best shown in FIG. 4, the plug 24 includes two prongs 26 which are adapted to engage with a pair of sockets 28 formed in the end wall of the housing 12. The sockets 28 are connected with an electrical circuit assembly, generally indicated at 30, which is mounted within the housing 12 between the front and back sections. The electrical circuit 30 may be constructed in accordance with the schematics illustrated in the aforesaid U.S. Pat. Nos. 3,938,507 or 4,535,783. A preferred embodiment is the circuitry disclosed in commonly assigned application, Ser. No. 07/172,924, filed Mar. 25, 1988. For present purposes, the disclosure of the two patents and the aforesaid application are hereby incorporated by reference into the present specification.

The electrical circuit 30 has connected therein a loudspeaker, generally indicated at 32, which is mounted within the housing 12 at a position spaced closely inwardly from a series of openings 34 formed in the front section 14. The front section 14 also includes a power on light 36 and certain switches which form a part of the electrical circuit such as a RECORD WITH NO SOUND switch 38, a RECORD WITH SOUND switch 40, a LIVE switch 42, and a PLAY BACK switch 43. With the switches shown, power is turned on by actuating any of the switches and holding it actuated for a few seconds. When the POWER ON light is lit indicating that the power is on, the power is turned off by actuating the LIVE switch and holding it for a few seconds. The POWER ON light 36 also provides a battery check for the batteries within the housing 12 which power the electrical circuit 30. The electrical circuitry 30 is provided with a memory having the capability of storing a predetermined time quantity of the electrical activity acquired by the electrodes 20 when used in accordance with the principles of the present invention. When the RECORD WITH NO SOUND switch 38 is actuated with the POWER ON light lit, the electrical activity being acquired by the electrodes 20 is recorded in the memory without any sound being produced in the loudspeaker. When the RECORD WITH SOUND switch is actuated, the electrical activity being acquired by the electrodes 20 is recorded in the memory with the electrical activity being simultaneously transmitted to the loudspeaker 32 as signals indicative of the acquired electrical activity. The PLAY BACK key 43 when operated is effective to play back the recorded electrical activity over the telephone line. When the LIVE switch 42 is actuated to turn the power on, the electrical activity at the electrodes 20 is transmitted over the line.

In accordance with the principles of the present invention, the electrodes 20 are constructed so that they are suitable for use in two modes. In the first mode, the electrodes 20 are extended away from the housing 12 by the electrical wires 22 and placed within the armpits in accordance with the teachings of the aforesaid U.S. Pat. No. 3,792,700. As shown, each electrode 20 is configured to be simply and conveniently engaged within an armpit of the user so as to be directly retained in the armpit between the upper arm and the chest of the user. As shown, each electrode 20 is formed of a plastic material having conductive particles embedded therein. An exemplary plastic is vinyl. Exemplary conductive particles are carbon particles.

As shown, each electrode 20 is of relatively thin configuration including opposed generally flat surfaces 44 and 46 of generally rectangular peripheral configurations with their corners rounded off. The flat surfaces 44 and 46 of each electrode 20 are defined by a periphery which is effectively L-shaped in cross-section so as to include a radial edge surface 48 facing toward the flat surface 46 and an axial edge surface 50 extending from the edge surface 48 to the flat surface 46. It will be noted that the flat surface 44 is generally rounded at its marginal periphery so as to merge with edge surface 50 so as not to present any outward sharp corners. Similarly, the juncture between the flat surface 46 and the edge surface 50 is also rounded but with less radius.

In accordance with the principles of the present invention, the back housing section 16 is formed with two spaced recesses 52, each of which is of a size and shape to accommodate an electrode. As shown, the peripheral wall defining each recess 52 is formed with a series of spaced electrode retaining projections 54. These peripheral projections 54 serve to engage the peripheral edge surface 50 of an associated electrode 20 so as to retain the same within the associated recess 52 with the radial edge surface 46 thereof engaging the adjacent outwardly facing surface of the housing section 16. In this way, the two electrodes 20 are removably mounted on the housing 12 in commonly outwardly facing spaced relation with respect to one another in operative positions fixed with respect to the housing 12. In this regard it will be noted that the smoother surfaces 44 face commonly outwardly so as to project beyond the outer surface of the housing section 16 engaged by the edge surfaces 48. In this way, the electrode surfaces 44 are presented in positions to engage the skin of the user in the chest area as shown in FIG. 1.

In order to control the position of wires 22 when the electrodes 20 are in their fixed operative positions within the recesses 52 in the exterior of the housing 12, the housing sections 14 and 16 are formed so as to provide a peripheral groove 56 which is spaced laterally from the recesses 52. The peripheral groove 56 communicates laterally with the recesses 52 through grooves 58 enabling the adjacent portion of the electrical wire 22 to extend to the associated electrode 20 when in its fixed operative position. The adjacent portion of each wire 22 is provided with indicia to indicate right armpit and left armpit. The insulation of each wire may be formed of a material similar to the electrodes so as to provide a body ground. A lateral groove 60 in the end wall of the housing 12 serves to receive the portion of the wires 22 adjacent the plug 24.

When the wires 22 are stored within the grooves 56, 58, and 60 and the electrodes 20 are disposed in their fixed positions within recesses 52 with respect to the housing 12, the user can simply grip the housing 12 with one hand and actuate the POWER ON light 36 and move the electrodes 20 with the housing 12 together into a position wherein the surfaces 44 of the electrodes 20 are in engagement with the skin of the chest, such as shown in solid lines in FIG. 1. As soon as this contact is made, the precordial electrical activity of the heart of the user is acquired in the electrodes for transmittal through the wires 22 to the electrical circuit 30. The acquired electrical activity is transmitted to the loudspeaker 32 as signals indicative of the heart activity which signals are capable of transmission over the telephone line.

Figure 5:
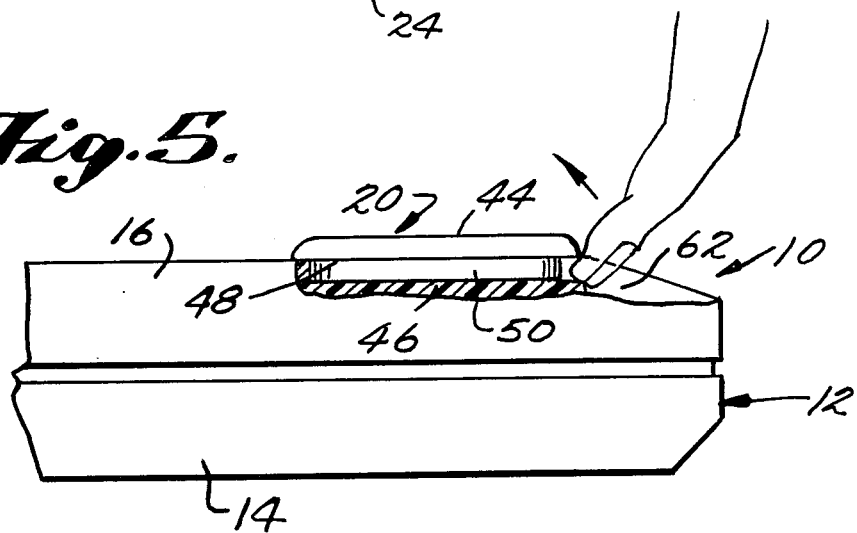
FIG. 5 is a fragmentary side elevational view of the device with certain parts broken away for purpose of clear illustration.

In a second mode, the electrodes 20 can be simply removed from their fixed operative positions and the wires 22 unwrapped from their storage position so that the electrodes can be extended away from the housing and be retained by the user in more widely spaced non-precordials as, for example, within the armpits as previously indicated. To facilitate removal of the electrodes 20 from the recesses 52, there is an end groove 62 formed in the ends of the back housing section 16 in communication with each recess. As best shown in FIG. 5, each groove 62 enables the user to engage a finger beneath a portion of the edge surface 48 of the associated electrode 20 so that a simple lifting action will readily disengage the peripheral edge surface 50 of the electrodes from the projections 54 enabling the electrode to be removed from the associated recess 52.

It will be understood that while the dual mode electrode arrangement of the present invention is particularly suitable for monitoring devices of the type for use under emergency conditions such as disclosed in the patents aforesaid, the arrangement provides a convenience and versatility to monitoring devices of the type which are simply used as a diagnostic tool to record and transmit heart activity events over the phone to a physician. Under these circumstances when an event is taking place, an emergency condition is presented in which the user must as rapidly as possible connect the monitor device to acquire the electrical activity of heart as the event is taking place. The memory of the unit is desirable under these circumstances to capture or record the electrical activity of the event as soon as possible at a time even before the user can reach the telephone.

It thus will be seen that the objects of this invention have been fully and effectively accomplished. It will be realized, however, that the foregoing preferred specific embodiments have been shown and described for the purpose of illustrating the functional and structural principles of this invention and are subject to change without departure from such principles. Therefore, this invention includes all modifications encompassed within the spirit and scope of the following claims.

What is claimed is:

1. A device suitable for use under emergency conditions for acquiring the electrical activity of the heart of a user in a form suitable for transmission over a telephonic line comprising:

a portable housing, a pair of electrodes operable when positioned in operative contacting relation with the skin of a user to acquire the electrical activity of the heart of the user, a pair of elongated electrical wires connected with said electrodes and with said housing for transmitting the electrical activity of the heart of the user acquired by said electrodes to said housing, sonic speaker means carried by said housing for creating signals indicative of the electrical activity acquired by the electrodes in a form suitable for transmission over a telephonic line, electric circuit means within said housing for transmitting the electrical activity acquired by said electrodes and transmitted by said pair of electrical wires to said sonic speaker means so as to create therein signals indicative of the electrical activity acquired by said electrodes for transmission over a telephonic line, means for removably mounting said electrodes on the exterior of said housing in outwardly facing spaced relation with respect to one another in operative positions fixed with respect to said housing so that said electrodes can be moved with the housing and retained in skin contacting relation with the chest of a user through manual engagement of said housing in housing retained positions with respect to the chest of the user so as to acquire precordial electrical activity of the heart of the user, said electrical wires being mounted on said housing so as to be operable to (1) transmit the precordial electrical activity acquired by said electrodes when in said housing retained positions, (2) enable said electrodes to be manually removed from said operative positions fixed with respect to said housing and extended from said housing into skin contacting relation with the user in directly retained operative positions spaced apart substantially greater than the spacing when in said housing retained positions so as to acquire non-precordial electrical activity of the heart of the user, and (3) transmit the non-precordial electrical activity acquired by said electrodes when in said directly retained operative positions.

2. A device as defined in claim 1 wherein said electrodes are configured to be placed within the armpits of a user and to be comfortably directly retained within the armpits by the user so that the non-precordial heart activity of the heart of the user acquired by said electrodes is between the armpits.

3. A device as defined in claim 2 wherein said electrodes are formed of plastic material impregnated with particles of a conductive material.

4. A device as defined in claim 3 wherein the particles of conductive material are carbon particles.

5. A device as defined in claim 4 wherein each of said electrodes is a relatively flat body having opposed planar surfaces defined peripherally by a peripheral edge, said peripheral edge including an edge surface facing toward one of said planar surfaces, said electrode mounting means including exterior surface means on said housing for releasably gripping the peripheral edge of each electrode so as to removably mount said electrodes in said fixed operative positions, the edge surfaces of said electrodes facing toward said housing when said electrodes are in said first operative positions, said housing having surface means enabling a user to digitally engage the edge surfaces of said electrodes when in said fixed operative positions to facilitate manual removal of the electrodes from said fixed operative positions.

6. A device as defined in claim 1 wherein said housing includes a peripheral groove in the exterior thereof within which said electrical wires are wrapped when said electrodes are in said fixed operative positions.

7. A device as defined in claim 1 wherein each of said electrodes is a relatively flat body having opposed planar surfaces defined peripherally by a peripheral edge, said peripheral edge including an edge surface facing toward one of said planar surfaces, said electrode mounting means including exterior surface means on said housing for releasably gripping the peripheral edge of each electrode so as to removably mount said electrodes in said fixed operative positions, the edge surfaces of said electrodes facing toward said housing when said electrodes are in said fixed operative positions, said housing having surface means enabling a user to digitally engage the edge surfaces of said electrodes when in said fixed operative positions to facilitate manual removal of the electrodes from said fixed operative positions.

8. A device as defined in claim 1 wherein said housing includes a peripheral groove in the exterior thereof within which said electrical wires are wrapped when said electrodes are in said fixed operative positions.

9. A device suitable for use under emergency conditions for acquiring the electrical activity of the heart of a user in a form suitable for transmission over a telephonic line comprising a portable housing, a pair of electrodes operable when positioned in operative contacting relation with the skin of a user to acquire the electrical activity of the heart of the user, means including at least one elongated electrical wire connected with one of said electrodes and with said housing for transmitting the electrical activity acquired by said electrodes to said housing, sonic speaker means carried by said housing for creating signals indicative of the electrical activity acquired by the electrodes in a form suitable for transmission over a telephonic line, electric circuit means within said housing for transmitting the electrical activity acquired by said electrodes and transmitted by said pair of electrical wires to said sonic speaker means so as to create therein signals indicative of the electrical activity acquired by said electrodes for transmission over a telephonic line, means for removably mounting said electrodes on the exterior of said housing in outwardly facing spaced relation with respect to one another in operative positions fixed with respect to said housing so that said electrodes can be moved with the housing and retained in skin contacting relation with the chest of a user through manual engagement of said housing in housing retained positions with respect to the chest of the user so as to acquire precordial electrical activity of the heart of the user, said electrical wire being mounted on said housing so as to be operable to (1) transmit the precordial electrical activity acquired by said electrodes when in said housing retained positions, (2) enable said one electrode to be manually removed from its operative position fixed with respect to said housing and extended from said housing into skin contacting relation with the user in a directly retained operative position spaced apart from the other electrode when retained in another operative position a distance substantially greater than the spacing distance when said electrodes are in said housing retained positions so as to acquire non-precordial electrical activity of the heart of the user, and (3) transmit the non-precordial electrical activity acquired by said electrodes when one electrode is in said directly retained operative position and the other electrode is in said another operative position.

* * * * *